US011916888B2

(12) United States Patent
McFarland et al.

(10) Patent No.: US 11,916,888 B2
(45) Date of Patent: *Feb. 27, 2024

(54) SYSTEMS AND METHODS FOR ENSURING DATA SECURITY IN THE TREATMENT OF DISEASES AND DISORDERS USING DIGITAL THERAPEUTICS

(71) Applicant: Click Therapeutics, Inc., New York, NY (US)

(72) Inventors: Ian McFarland, San Francisco, CA (US); Davina Pallone, San Francisco, CA (US); Jason F. Ma, San Francisco, CA (US); Daniel Barbosa, San Francisco, CA (US); Phu Trinh, Alameda, CA (US)

(73) Assignee: Click Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/298,856

(22) Filed: Apr. 11, 2023

(65) Prior Publication Data
US 2023/0254293 A1 Aug. 10, 2023

Related U.S. Application Data

(63) Continuation of application No. 17/201,879, filed on Mar. 15, 2021, now Pat. No. 11,658,946, which is a
(Continued)

(51) Int. Cl.
*H04L 9/40* (2022.01)
*G06F 21/60* (2013.01)
(Continued)

(52) U.S. Cl.
CPC ........ *H04L 63/0428* (2013.01); *G06F 21/602* (2013.01); *G06F 21/6245* (2013.01);
(Continued)

(58) Field of Classification Search
CPC ............. H04L 63/0428; H04L 63/0407; H04L 63/0823; G06F 21/602; G06F 21/6245;
(Continued)

(56) References Cited

U.S. PATENT DOCUMENTS

2007/0192139 A1    8/2007  Cookson et al.
2008/0015553 A1*   1/2008  Zacharias ............... A61F 9/008
                                                          606/4
(Continued)

FOREIGN PATENT DOCUMENTS

AU    2014202823 A1    12/2014
CN       1387653 A     12/2002
(Continued)

OTHER PUBLICATIONS

International Search Report for International Application No. PCT/US2018/055120 dated Feb. 8, 2019.
(Continued)

*Primary Examiner* — Samson B Lemma
(74) *Attorney, Agent, or Firm* — Foley & Lardner LLP

(57) ABSTRACT

A method that includes receiving patient-generated event data over a network from a patient device associated with a patient having an active digital therapy prescription for treating an underlying disease or disorder. The patient-generated event data is encrypted by the patient device and includes at least one timestamped event related to the active digital therapy prescription. In response to receiving the patient-generated event data, the method includes decrypting, anonymizing, and storing the anonymized patient-generated event data on memory hardware. The method further includes receiving a patient record request over the network from a healthcare provider (HCP) system that requests the patient-generated event data and includes an authentication token. In response to receiving the patient record request, the
(Continued)

method includes retrieving and encrypting the anonymized patient-generated event data from the memory hardware using the authentication token. The method also includes transmitting the encrypted patient-generated event data to the HCP system.

20 Claims, 8 Drawing Sheets

Related U.S. Application Data continuation of application No. 16/156,373, filed on Oct. 10, 2018, now Pat. No. 10,986,071.

(60) Provisional application No. 62/671,131, filed on May 14, 2018, provisional application No. 62/570,975, filed on Oct. 11, 2017.

(51) Int. Cl.
| | | |
|---|---|---|
| *G06F 21/62* | (2013.01) | |
| *G16H 10/60* | (2018.01) | |
| *G16H 20/10* | (2018.01) | |
| *G16H 20/13* | (2018.01) | |
| *G16H 80/00* | (2018.01) | |

(52) U.S. Cl.
CPC ......... *G06F 21/6254* (2013.01); *G16H 10/60* (2018.01); *G16H 20/10* (2018.01); *G16H 20/13* (2018.01); *G16H 80/00* (2018.01); *H04L 63/0407* (2013.01); *H04L 63/0823* (2013.01)

(58) Field of Classification Search
CPC .... G06F 21/6254; G16H 20/10; G16H 20/13; G16H 10/60; G16H 80/00
USPC .......................................................... 726/17
See application file for complete search history.

(56) References Cited

U.S. PATENT DOCUMENTS

| | | | | |
|---|---|---|---|---|
| 2011/0119075 | A1* | 5/2011 | Dhoble ................. | G16H 10/60 |
| | | | | 705/2 |
| 2012/0129139 | A1* | 5/2012 | Partovi ................. | G16H 40/67 |
| | | | | 434/262 |
| 2013/0124523 | A1* | 5/2013 | Rogers ................. | G16H 10/60 |
| | | | | 707/741 |
| 2014/0164022 | A1* | 6/2014 | Reed ..................... | G16H 40/63 |
| | | | | 705/3 |
| 2015/0254416 | A1* | 9/2015 | Shih ..................... | G16H 80/00 |
| | | | | 705/2 |
| 2015/0347701 | A1* | 12/2015 | Atkin .................... | G16H 10/40 |
| | | | | 705/2 |
| 2016/0147945 | A1* | 5/2016 | MacCarthy .......... | H04W 12/02 |
| | | | | 705/51 |
| 2016/0314279 | A1* | 10/2016 | Slepian ................. | G06T 11/206 |
| 2016/0350481 | A1* | 12/2016 | Wesemann ............ | G16H 10/60 |
| 2017/0161439 | A1* | 6/2017 | Raduchel ............. | G16H 10/60 |
| 2017/0177798 | A1* | 6/2017 | Samuel ................. | H04L 67/12 |
| 2019/0147043 | A1* | 5/2019 | Moskowitz ........... | A61B 5/165 |
| | | | | 704/9 |
| 2019/0182193 | A1 | 6/2019 | Moskowitz | |
| 2019/0260703 | A1 | 8/2019 | Moskowitz | |
| 2020/0000389 | A1 | 1/2020 | Moskowitz | |

FOREIGN PATENT DOCUMENTS

| | | |
|---|---|---|
| CN | 1810030 A | 7/2006 |
| CN | 101339586 A | 1/2009 |
| CN | 102750430 A | 10/2012 |
| CN | 103136716 A | 6/2013 |
| CN | 105095622 A | 11/2015 |
| CN | 105636028 A | 6/2016 |
| CN | 105706096 A | 6/2016 |
| EP | 3131030 A1 | 2/2017 |
| JP | 2001052079 A | 2/2001 |

OTHER PUBLICATIONS

China National Intellectual Property Administration, Office Action for Application No. 201880066113.8 dated Feb. 11, 2023.
European Patent Office, Examination Report for Application No. 18866387.6 dated Mar. 22, 2023.
He Kai et al: "Efficient Fine-Grained Access Control for Secure Personal Health Records in Cloud Computing", Sep. 21, 2016, ICIAP: International Conference on Image Analysis and Processing, 17th International Conference, Naples, Italy, Sep. 9-13, 2013. Proceedings; [Lecture Notes in Computer Science; Lect. Notes Computer], Springer, Berlin, Heidelberg, pp. 65-79, XP047356907, ISBN: 978-3-642-173 18-9 [retrieved on Sep. 21, 2016].

* cited by examiner

SYSTEMS AND METHODS FOR ENSURING DATA SECURITY IN THE TREATMENT OF DISEASES AND DISORDERS USING DIGITAL THERAPEUTICS

CROSS REFERENCE TO RELATED APPLICATIONS

This U.S. patent application is a continuation of, and claims priority under 35 U.S.C. § 120 from, U.S. patent application Ser. No. 17/201,879, filed on Mar. 15, 2021, which is a continuation of, and claims priority under 35 U.S.C. § 120 from, U.S. patent application Ser. No. 16/156,373, filed on Oct. 10, 2018, which issued as U.S. Pat. No. 10,986,071, and which claims priority under 35 U.S.C. § 119(e) to U.S. Provisional Application 62/570,975, filed on Oct. 11, 2017, and U.S. Provisional Application 62/671,131, filed on May 14, 2018. The disclosures of these prior applications are considered part of the disclosure of this application and are hereby incorporated by reference in their entireties.

TECHNICAL FIELD

This disclosure relates to systems and methods for ensuring data security in the treatment of diseases and disorders using digital therapeutics.

BACKGROUND

Drug therapy has played a significant role in the treatment of various medical diseases and disorders. Traditional drug therapy involves the administration of pharmaceuticals and the like. Examples of conventional pharmaceuticals may include small-molecule drugs, which are usually derived from chemical synthesis, and biopharmaceuticals, which may include recombinant proteins, vaccines, blood products used in therapeutically gene therapy, monoclonal antibodies, cell therapy, and the like. While drug therapy has proven to be an effective mechanism for treating certain diseases and disorders, it is not without drawbacks. For example, pharmaceuticals are known to come with certain, frequently undesirable, side-effects. In addition, pharmaceuticals are often costly—sometimes prohibitively so.

Recently, there is a steady rise in the treatment of many medical diseases and disorders through the use of mechanisms in addition to, or in lieu of, the aforementioned traditional drug therapies. Specifically, as digital communication and cloud computing technologies continue to advance and gain acceptance in the medical community, the use of digital therapeutics is an effective form of treatment to combat medical diseases and disorders. As with any form of digital communication, digital therapeutics must place a very strong emphasis to ensure that patients' data is secure and use of the data complies with various laws and regulations.

SUMMARY

One aspect of the disclosure provides a method for treating a patient with a disease or disorder using digital therapeutics. The method includes receiving, at data processing hardware of a backend service, patient-generated event data over a network from a patient device associated with the patient having an active digital therapy prescription prescribed by a supervising healthcare professional (HCP) for treating the underlying disease or disorder, the patient-generated event data encrypted by the patient device and including at least one timestamped event related to the active digital therapy prescription. In response to receiving the patient-generated event data, the method includes decrypting, by the data processing hardware, the patient-generated event data; anonymizing, by the data processing hardware, the patient-generated event data by removing any patient identifying information from the patient-generated event data; and storing, by the data processing hardware, the anonymized patient-generated event data on memory hardware of the backend service in communication with the data processing hardware. The method further includes receiving, at the data processing hardware, a patient record request over the network from a HCP system associated with the HCP supervising the patient. The patient record request requests the patient-generated event data and includes an authentication token. In response to receiving the patient record request, the method includes retrieving, by the data processing hardware, the anonymized patient-generated event data from the memory hardware using the authentication token and encrypting, by the data processing hardware, the patient-generated event data. The method also includes transmitting, by the data processing hardware, the encrypted patient-generated event data over the network to the HCP system. The encrypted patient-generated event data when received by the HCP system causes the HCP system to decrypt the patient-generated event data and present the patient-generated event data in a patient dashboard screen of a display of the HCP system.

Implementations of the disclosure may include one or more of the following optional features. In some implementations, the method further includes, prior to receiving the patient-generated event data, receiving, at the data processing hardware, a registration request from the patient device. The registration request includes an access code and requests the patient to register the patient device with a patient application for accessing the digital therapy prescription. In these implementations, the method further includes determining, by the data processing hardware, whether the access code is valid, and when the access code is valid, prompting, by the data processing hardware, the patient to register the patient device with the patient application. The method may further include receiving, at the data processing hardware an add patient input from the HCP system. Here, the add patient input enrolls the patient for access to the digital therapy prescription for treating the underlying disease or disorder. The add patient input includes an email address of the patient. The method may then include transmitting an enrollment verification email from the data processing hardware to the patient device using the email address of the patient. The enrollment verification email includes the access code and instructs the patient to input the access code to transmit the registration request.

In some implementations, the patient device executes a patient application configured to detect when a patient-generated event related to the active digital therapy prescription occurs, and determine whether the network connectivity between the patient device and the backend service is available. When network connectivity is available, the patient application is further configured to instruct the patient device to transmit the patient-generated event over the network to the data processing hardware, wherein the patient-generated event is timestamped and includes the patient-generated event data. In some examples, when the network connectivity is unavailable, the patient application is configured to timestamp the patient-generated event, store the patient-generated event in an encrypted queue of memory hardware of the patient device, and transmit the patient-generated event data from the encrypted queue to the backend service when the network connectivity is available.

In some examples, retrieving the anonymized patient-generated event data from the memory hardware using the authentication token includes identifying the anonymized patient-generated event data by matching cryptographic hashes associated with the authenticated token and the anonymized patient-generated event data. In some examples, the backend service operates within virtualized containers providing a secure execution environment for the backend service.

In some implementations, the method further includes receiving, at the data processing hardware, a therapy content request from the patient device that requests therapy content related to the digital therapy prescription of the patient, and retrieving, by the data processing hardware, the requested therapy content related to the digital therapy prescription of the patient from the memory hardware. In these implementations, after retrieving the requested therapy content, the method further includes transmitting, by the data processing hardware, the therapy content to the patient device. The therapy content when received by the patient device causes a patient application executing on the patient device to visually and/or audibly output the therapy content from the patient device. The therapy content may include a learning module including a series of therapy lessons the patient has to complete during a duration of the digital therapy prescription. The one or more therapy lessons in the therapy content may correspond to a cognitive behavioral therapy learning portion of the digital therapy prescription for treating the underlying disease or disorder. In some examples, when the therapy content includes the learning module including the series of therapy lessons, the series of therapy lessons are arranged in an ordered list that must be completed by the patient in order one at a time. Additionally or alternatively, at least one of the therapy lessons may include a corresponding proficiency test related to the therapy lesson that the patient must successfully pass in order to complete the corresponding therapy lesson. The therapy content may further include audio and/or video files associated with the learning module.

In some implementations, the patient-generated event data includes a drug screen result for the patient indicating whether or not the patient used a substance. The patient-generated event data may additionally or alternatively include a self-reported update indicating whether or not the patient used a particular substance. In some examples, the patient-generated event data includes a log in event to a patient application executing on the patient device. Here, the patient application is configured to initiate communication over the network between the patient device and the backend service and to provide access to the digital therapy prescription.

Another aspect of the disclosure provides a system for treating a patient with a disease or disorder using digital therapeutics. The system includes data processing hardware and memory hardware in communication with the data processing hardware. The memory hardware stores instructions that when executed by the data processing hardware cause the data processing hardware to perform operations that include receiving patient-generated event data over a network from a patient device associated with the patient having an active digital therapy prescription prescribed by a supervising healthcare professional (HCP) for treating the underlying disease or disorder, the patient-generated event data encrypted by the patient device and including at least one timestamped event related to the active digital therapy prescription. In response to receiving the patient-generated event data, the operations further include decrypting the patient-generated event data; anonymizing the patient-generated event data by removing any patient identifying information from the patient-generated event data; and storing the anonymized patient-generated event data on the memory hardware. The operations further include receiving a patient record request over the network from a HCP system associated with the HCP supervising the patient. The patient record request requests the patient-generated event data and includes an authentication token. In response to receiving the patient record request, the operations further include retrieving the anonymized patient-generated event data from the memory hardware using the authentication token and encrypting the patient-generated event data. The operations also include transmitting the encrypted patient-generated event data over the network to the HCP system. The encrypted patient-generated event data when received by the HCP system causes the HCP system to decrypt the patient-generated event data and present the patient-generated event data in a patient dashboard screen of a display of the HCP system.

Implementations of the disclosure may include one or more of the following optional features. In some implementations, the operations further include, prior to receiving the patient-generated event data, receiving a registration request from the patient device. The registration request includes an access code and requests the patient to register the patient device with a patient application for accessing the digital therapy prescription. In these implementations, the operations further include determining whether the access code is valid, and when the access code is valid, prompting the patient to register the patient device with the patient application. The operations may further include receiving an add patient input from the HCP system. Here, the add patient input enrolls the patient for access to the digital therapy prescription for treating the underlying disease or disorder. The add patient input includes an email address of the patient. The operations may then include transmitting an enrollment verification email from the data processing hardware to the patient device using the email address of the patient. The enrollment verification email includes the access code and instructs the patient to input the access code to transmit the registration request.

In some implementations, the patient device executes a patient application configured to detect when a patient-generated event related to the active digital therapy prescription occurs, and determine whether the network connectivity between the patient device and the backend service is available. When network connectivity is available, the patient application is further configured to instruct the patient device to transmit the patient-generated event over the network to the data processing hardware, wherein the patient-generated event is timestamped and includes the patient-generated event data. In some examples, when the network connectivity is unavailable, the patient application is configured to timestamp the patient-generated event, store the patient-generated event in an encrypted queue of memory hardware of the patient device, and transmit the patient-generated event data from the encrypted queue to the backend service when the network connectivity is available.

In some examples, retrieving the anonymized patient-generated event data from the memory hardware using the authentication token includes identifying the anonymized patient-generated event data by matching cryptographic hashes associated with the authenticated token and the anonymized patient-generated event data. In some examples, the backend service operates within virtualized containers providing a secure execution environment for the backend service.

In some implementations, the operations further include receiving a therapy content request from the patient device that requests therapy content related to the digital therapy prescription of the patient, and retrieving the requested therapy content related to the digital therapy prescription of the patient from the memory hardware. In these implementations, after retrieving the requested therapy content, the operations further include transmitting the therapy content to the patient device. The therapy content when received by the patient device causes a patient application executing on the patient device to visually and/or audibly output the therapy content from the patient device. The therapy content may include a learning module including a series of therapy lessons the patient has to complete during a duration of the digital therapy prescription. The one or more therapy lessons in the therapy content may correspond to a cognitive behavioral therapy learning portion of the digital therapy prescription for treating the underlying disease or disorder. In some examples, when the therapy content includes the learning module including the series of therapy lessons, the series of therapy lessons are arranged in an ordered list that must be completed by the patient in order one at a time. Additionally or alternatively, at least one of the therapy lessons may include a corresponding proficiency test related to the therapy lesson that the patient must successfully pass in order to complete the corresponding therapy lesson. The therapy content may further include audio and/or video files associated with the learning module.

In some implementations, the patient-generated event data includes a drug screen result for the patient indicating whether or not the patient used a substance. The patient-generated event data may additionally or alternatively include a self-reported update indicating whether or not the patient used a particular substance. In some examples, the patient-generated event data includes a log in event to a patient application executing on the patient device. Here, the patient application is configured to initiate communication over the network between the patient device and the backend service and to provide access to the digital therapy prescription.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
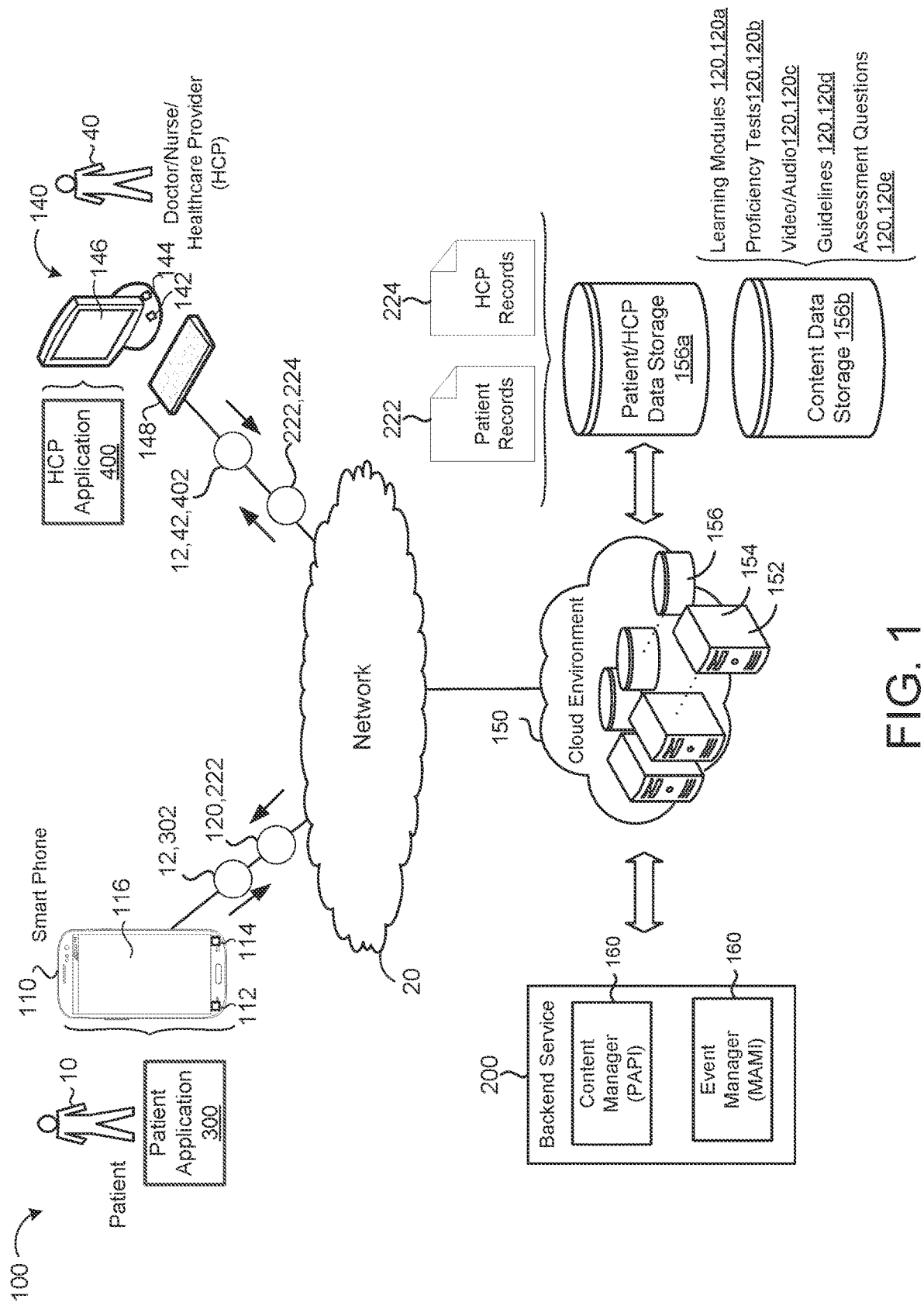
FIG. 1 is a schematic view of an example system of using digital therapeutics to treat a patient with a disorder or disease.

Implementations herein are directed toward using digital therapeutics tailored to treat specific diseases and/or disorders. Digital therapeutics allow a patient to spend more time in therapy, and at a reduced cost, compared to if the patient had to meet with a healthcare professional (e.g., physician, nurse, clinician, etc.) in person during scheduled appointments. Electronic computing devices, such as smartphones and tablets, allow a patient to access, via download and/or streaming, therapeutic content specifically tailored to treat a disease/disorder associated with the patient, as well as promote the patient to take an active role in engaging with the therapeutic content. For instance, the therapeutic content may include learning modules that educate the patient about his or her disease/disorder and how to treat the disease/disorder. These learning modules may include any combination of video, audio, treatment guidelines, and/or interactive content, such as assessment questions or quizzes that test the patient's understanding and knowledge obtained from the learning modules. Additionally, the therapeutic content may include usage guidelines for one or more prescribed medications to treat the patient's disease/disorder. The patient may be rewarded through notifications and/or electronic rewards (e.g., gift cards) when the patient successfully completes learning modules, follows usage guidelines for prescribed medications, and/or otherwise follows treatment guidelines prescribed to treat the patient's disease/disorder.

The patient's progress and interaction with the therapeutic content, as well as subjective data, may be logged and securely stored by a backend service. Subjective data may include a patient with a substance abuse disorder indicating that he/she has cravings to use a specific substance, has used the specific substance, and/or results from a drug screen for the specific substance. All patient health information (PHI) and patient identifying information (PII) may be encrypted and transmitted over a network via Hyper Text Transfer Protocol Secure (HTTPS) to the backend service and the backend service may further separate the PHI from the PII before logging the information. Advantageously, the PHI becomes de-identified when stored by the backend service so that any of the PII identifying the patient is not linked to the PHI, thereby providing a high-level of privacy and security to patient sensitive data. Accordingly, each event outlining patient activity with the therapeutic content and subjective content recorded by the patient can be logged by the backend service in a secure and private manner, and analyzed to determine the patient's progress, as well as compliance, with the therapy prescribed to the patient. Moreover, the backend service can perform analytics on de-identified health information from a patient population to determine how effective the therapeutic content is at treating specific disorders/diseases without identifying any of the patients with that disorder/disease. For instance, the backend service may analyze de-identified health information from a patient population with schizophrenia to see if the patients are actively engaging with the therapeutic content for treating schizophrenia, as well as if the patients are following specific guidelines prescribed to those patients such as taking prescribed medications in which the patients are less than enthusiastic about ingesting/administering.

The patients may access the therapy content when a healthcare professional (HCP) prescribes a digital therapy prescription to the patient for treating the specific disease or disorder. For instance, during an initial consultation or re-occurring appointment (e.g., every month) the HCP may prescribe the digital therapy prescription to the patient by providing the patient with an access code to access the prescription from the backend service. The HCP may enroll the patient with the backend service and the backend service may send a verification email that includes the access code and instructs the patient to verify enrollment by inputting the access code. The HCP, through the use of similar electronic computing devices, may monitor the progress of a list of patients under the supervision of the HCP in which the HCP has prescribed digital therapy prescriptions by accessing backend service. Here, the HCP may provide appropriate credentials (e.g., an authentication token) to the backend service in order to authenticate the HCP and verify that the HCP is authorized to access the patients' health information and patient-generated events logged by the backend service and associated with the patient's engagement and compliance with their digital therapy prescriptions. Once the HCP is authenticated and authorized, the backend service may retrieve the de-identified health information logged by each of the patients and re-identify the retrieved health information for each patient with the associated patient identifying information and send the patient health information for each patient to the HCP's electronic device. For instance, the HCP may access a webpage that displays a dashboard of the PHI for each patient prescribed digital therapy prescriptions under the supervision of the HCP. All communications between the HCP and the backend service may be encrypted and transmitted using secure protocols such as HTTPS. In some examples, the backend service may never re-identify the de-identified health information and simply send the PII and the de-identified health information to the HCP separately and the HCP may re-identify the health information locally so that patient anonymity is maintained at the backend service. Here, the HCP may have access to a client-side key never exposed to the backend service for use in re-identifying the patient health information. Additionally, the same or different client-side key may permit only the HCP to decrypt encrypted patient data sent by the backend service over the network.

Referring to FIG. 1, in some implementations, a therapy prescription system 100 provides a patient 10 access to a digital therapy prescription 225 (FIG. 2A) prescribed to the patient 10 and monitors events associated with the patient's 10 interaction with the digital therapy prescription 225. As used herein, the patient 10 is located at some remote location, such as the patient's 10 residence or place of employment. The system 100 can provide access to numerous therapy prescriptions, each specifically tailored for treating a particular disease or disorder. For instance, for a patient 10 with a substance abuse disorder, an authorized healthcare professional (HCP) 40 supervising the patient may prescribe the patient a digital therapy prescription that includes therapy content 120 designed to educate the patient and provide the necessary tools (e.g., cognitive behavior changes) to treat their substance abuse disorder. Similarly, digital therapy prescriptions are available for treating patients 10 with diseases such as schizophrenia. The HCP 40 may include a physician, nurse, clinician, or other health professional qualified for treating the patient's 10 underlying diseases/disorder.

In some examples, the system 100 includes a network 20, a patient device 110, an HCP system 140, and a backend service 200. The network 20 provides access to cloud computing resources 150 (e.g., distributed system) that execute the backend service 200 to provide for the performance of services on remote devices instead of specific modules. Accordingly, the network 20 allows for interaction between patients 10 and HCPs 40 with the backend service 200. For instance, the backend service 200 may receive data 12 inputted by the patient 10 and allow the patient 10 and/or HCP 40 supervising the patient 10 to retrieve previously inputted data 12 stored on a storage system (e.g., cloud storage resources 156, memory hardware 144 of the HCP system 140, and/or memory hardware 114 of the patient device 110) for output on a display 116, 146.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the HCP system 140, and the backend service 200 communicate with each other by sending and receiving signals (wired or wireless) via the network 20. In some examples, the network 20 provides access to cloud computing resources, which may be elastic/on-demand computing and/or storage resources 156 available over the network 20. The term 'cloud' services generally refers to a service performed not locally on a user's device, but rather delivered from one or more remote devices accessible via one or more networks 20.

The patient device 110 may include, but is not limited to, a portable electronic device (e.g., smartphone, cellular phone, personal digital assistant, personal computer, or wireless tablet device), a desktop computer, or any other electronic device capable of sending and receiving information via the network 20. The patient device 110 includes data processing hardware 112 (a computing device that executes instructions), memory hardware 114, and a display 116 in communication with the data processing hardware 112. In some examples, the patient device 110 includes a keyboard 148, mouse, microphones, and/or a camera for allowing the patient 10 to input data. In addition to or in lieu of the display 116, the patient device 110 may include one or more speakers to output audio data to the patient 10. For instance, audible alerts may be output by the speaker to notify the patient 10 when it is time to ingest a medication prescribed to the patient 10 in the digital therapy prescription or otherwise notify the patient 10 about some time sensitive event associated with the digital therapy prescription. In some implementations, the patient device 110 executes a patient application 300 (or accesses a web-based patient application) for establishing a connection with the backend service 200 to input and retrieve data 12 therefrom. For instance, the patient 10 may have access to the patient application 300 for a duration (e.g., 3 months) of the digital therapy prescription prescribed to the patient 10. Here, the patient device 110 may launch the application 300 by initially providing an access code 302 when the digital therapy prescription is prescribed by the HCP 40 that allows the patient 10 to onboard patient data 12 to the backend service 200 and retrieve therapy content 120 from the backend service 200 that is specifically tailored for treating the patient's 10 disease/disorder. The patient data 12 may include patient identifying information (PII) that identifies the patient (e.g., name, age, gender, email address, demographic, etc.) and patient health information (PHI) that indicates patient's 10 health (e.g., diseases/disorders, treatment history, prescriptions, medications, etc.). Described in greater detail below, the backend service 200 is configured to anonymize the PHI aspect of the patient data 12 input by each patient 10 (or their supervising HCPs 40) so that the PII is no longer linked to the PHI while stored on the storage resources 156 of the cloud computing system 150. This ensures that the PHI is anonymized from even employees or operators of an entity providing the backend service 200. The storage resources 156 may provide data storage 156a for storing the patient data 12 in a corresponding patient record 222. The patient record 222 may be stored so that the PHI is anonymized, but may later re-identify the PHI with the PII when the patient 10 or supervising HCP 40 requests the patient record 222. All data transmitted over the network 20 between the patient device 110 and the cloud computing system 150 may be encrypted and sent over secure communication channels. For instance, the patient application 300 may encrypt patient data 12 before transmitting to the backend service 200 via the HTTPS protocol and decrypt a patient record 222 received from the backend service 200. When network connectivity is not available, the patient application 300 may store the patient data 12 in an encrypted queue within the memory hardware 114 until network connectivity is available.

The patient device 110 may execute or access the patient application 300 to retrieve therapy content 120 associated with the digital therapy prescription prescribed to the patient 10 for treating the patient's 10 disease/disorder. The storage resources 156 may provide content data storage 156b for storing therapy content 120. For instance, the therapy content 120 may include learning modules 120a, proficiency tests 120b, video/audio 120c, application guidelines 120d, and/or assessment questions 120e. The learning modules 120a may include a series of therapy lessons that educate the patient 10 about his or her disease/disorder and informs the patient 10 on how to treat the disease/disorder. The proficiency tests 120b may indicate the patient's 10 understanding of each lesson in a learning module 120a before the patient 10 is able to access a next learning module. For example, a learning module 120a may be designated for each step of a twelve-step program for a patient 10 being treated for a substance abuse disorder and each therapy lesson may cover one or some other subset of the twelve steps. The video/audio 120c may include videos or audio files associated with the learning modules 120a. The application guidelines 120d may include detailed instructions for using the patient application 300. Application guidelines 120d could further include a video or slide deck that shows the patient 10 how to navigate the patient application 300 and perform specific functions. The assessment questions 120e may include specific questions 120e that seek to extract information about the patient's 10 progress and well-being during treatment. For instance, the same or different questions 120e may be provided to the patient 10 on a weekly basis until the digital therapy prescription expires.

The HCP system 140 may be located at a clinic, doctor's office, or facility administered by the HCP 40 and includes data processing hardware 142, memory hardware 144, and a display 146. The memory hardware 144 and the display 146 are in communication with the data processing hardware 142. For instance, the data processing hardware 142 may reside on a desktop computer or portable electronic device for allowing the HCP 40 to input and retrieve data to and from the backend service 200. In some examples, the HCP 40 may initially onboard some or all of the patient data 12 at the time of prescribing the digital therapy prescription to the patient 10. As with the patient device 110, the HCP system 140 includes a keyboard 148, mouse, microphones, speakers and/or a camera. In some implementations, the HCP system 140 (i.e., via the data processing hardware 142) executes a HCP application 400 (or accesses a web-based patient application) for establishing a connection with the backend service 200 to input and retrieve data therefrom. For instance, the HCP system 140 may be able to access the anonymized patient records 222 securely stored by the backend service 200 on the storage resources 156 by providing an authentication token 402 validating that the HCP 40 is supervising the patient 10 and authorized to access the corresponding patient record 222. The HCP application 400 may store a corresponding authentication token 402 on the memory hardware 144 of the HCP system 140 for each patient 10 under the supervision of the HCP 40 and having a digital therapy prescription that is currently active. The authentication token 402 may define what patient data 12 the HCP system 140 is permitted to obtain from the backend service 200. For instance, the authentication token 402 may be associated with a specific therapy prescription, and therefore may only permit the HCP system 140 to retrieve patient data 12 from the patient record 222 that is related to that digital therapy prescription. Thus, the backend service 200 may only extract specific patient data 12 from the patient record 222 that is within a scope defined by the corresponding authentication token 402. The HCP system 140 may further input HCP data 42 that identifies the HCP 40, provides a list of patients 10 under the supervision of the HCP 40 and prescribed digital therapy prescriptions by the HCP 40, and other information associated with the HCP 40 (e.g., hospital/practice affiliation, credentials, etc.). The storage resources 156 may provide the data store 156a to store the HCP data 42 in a corresponding HCP record 224.

The cloud computing resources 150 may be a distributed system (e.g., remote environment) having scalable/elastic resources 152. The resources 152 include computing resources 154 (e.g., data processing hardware) and/or the storage resources 156 (e.g., memory hardware). The cloud computing resources 150 execute the backend service 200 for facilitating communications with the patient device 110 and the HCP system 140 and storing data on the storage resources 156 within patient/HCP data store 156a and/or the content data store 156b. In some examples, the backend service 200 and the data stores 156a, 156b reside on a standalone computing device. The backend service 200 may provide the patient 10 with the patient application 300 (e.g., a mobile application, a web-site application, or a downloadable program that includes a set of instructions) executable on the data processing hardware 112 and accessible through the network 20 via the patient device 110 when the patient 10 provides a valid access code 302. Similarly, the backend service 200 may provide the HCP 40 with the HCP application 400 (e.g., a mobile application, a web-site application, or a downloadable program that includes a set of instructions) executable on the data processing hardware 142 and accessible through the network 20 via the HCP system 140.

The backend service 200 contains various service layers that are fundamental to efficiency and security of data associated with digital therapy prescriptions prescribed to patients 10. Described in greater detail below, data associated with each digital therapy prescription includes, without limitation, the patient data 12; the HCP data 42; patient use of learning modules 120a and other therapy content 120; patient events of drug screens, substance use, cravings, and craving triggers; and HCP reports on patient compliance with the digital therapy prescription. The backend service 200 facilitates all communications between the patient and HCP applications 300, 400, and ensures security for all data stored across the storage resources 156, as well as all data transmitted over the network 20 to and from the patient and HCP applications 300, 400. In some examples, all the data stored across the storage resources is Advanced Encryption Standard (AES) encrypted on-device, and all communication over the network 20 is Transport Layer Security (TLS) or HTTPS encrypted.

In the example shown, the backend service 200 implements a content manager 210 and an event manager 220 that operate as frontends to the storage resources 156. The content manager 210 may include an Application Programming Interface (API) for operating as a two-way communicator that provides transmit/receive relationships with the applications 300, 400, facilitates management and storage of therapy content 120, patient data 12, and HCP data 42. The event manager 220, on the other hand, is a one-way communicator that receives immutable event data from the applications 300, 400 for storage on the storage resources 156. In some configurations, the content manager 210 and the event manager 220 each execute in a secure execution environment running on dedicated redundant instances (e.g., web service containers). For instance, the content manager 210 and the event manager 220 (and optionally the patient application 300 and/or the HCP application 400 when accessed as web-based applications) may operate within virtualized Docker containers to ensure that the runtime environment is consistent across development, testing, verification and validation, and production environments. Using these Docker containers may also ensure that the runtime environment is revision-controlled according to development standards of an entity providing the system 100 and the backend service 200. As such, the content manager 210 and the event manager 220 may only be accessible to external callers through secured, software mediated interfaces, and may only be accessible via HTTPS. Further communications between the content manager 210 and the event manager 220 may be further secured through AES-encrypted session tokens for use in identifying all actors in the system 100 without providing any data visibility to untrusted third parties.

Figure 5:
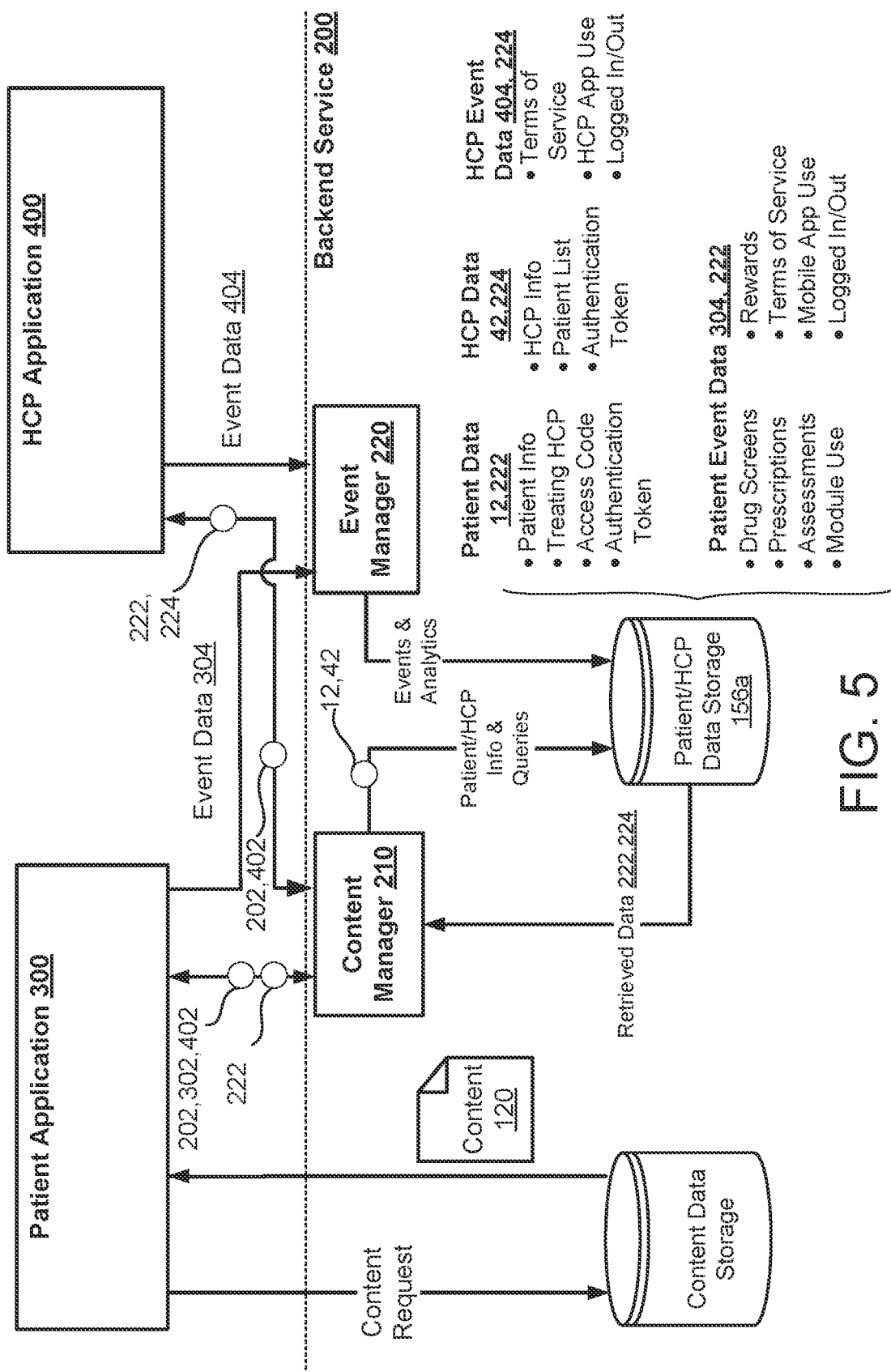
FIG. 5 is a schematic view showing a content manager and an event manager cooperating to store and retrieve patient-generated event data.

In some examples, the content manager 210 corresponds to a central web services engine for the backend service 200 by managing access and control and facilitating storage of all mutable state information about patients 10, HCPs 40, and their relationships. The content manager 210 may additionally provide mediated client access to analytics data stored by the event manager 220 as immutable time series event data 304 (FIG. 5). The content manager 210 may be implemented in JavaScript, using Node as its primary runtime framework.

The event manager 220 is responsible for storing time series event data 304, 404 (FIG. 5) within the system 100. For instance, the event manager 220 may store events tied to individual patients 10 and HCPs 40 in the system 100 as programmatically immutable data that is retained in perpetuity. In other words, the event manager 220 functions as a sink for patient- and HCP-generated events 304, 404 such as, without limitations, self-reported substance use, HCP-reported appointment compliance, and other events of use of therapy content 120. The event manager 220 may further immutably store and update the patient records 222 and HCP records 224 to provide an audit trail indicating HCP-initiated updates to the digital therapy prescription 225 prescribed to the patient 10 and/or modifications to the patient record 222. In some implementations, the event manager 220 resides on a JavaScript/node.js application layer and writes events to the patient/HCP data store 156a. In these implementations, the content manager 210 is operative as a query interface that interacts with the patient and HCP applications 300, 400 to retrieve immutable data stored by the event manager 220.

Figure 2A:
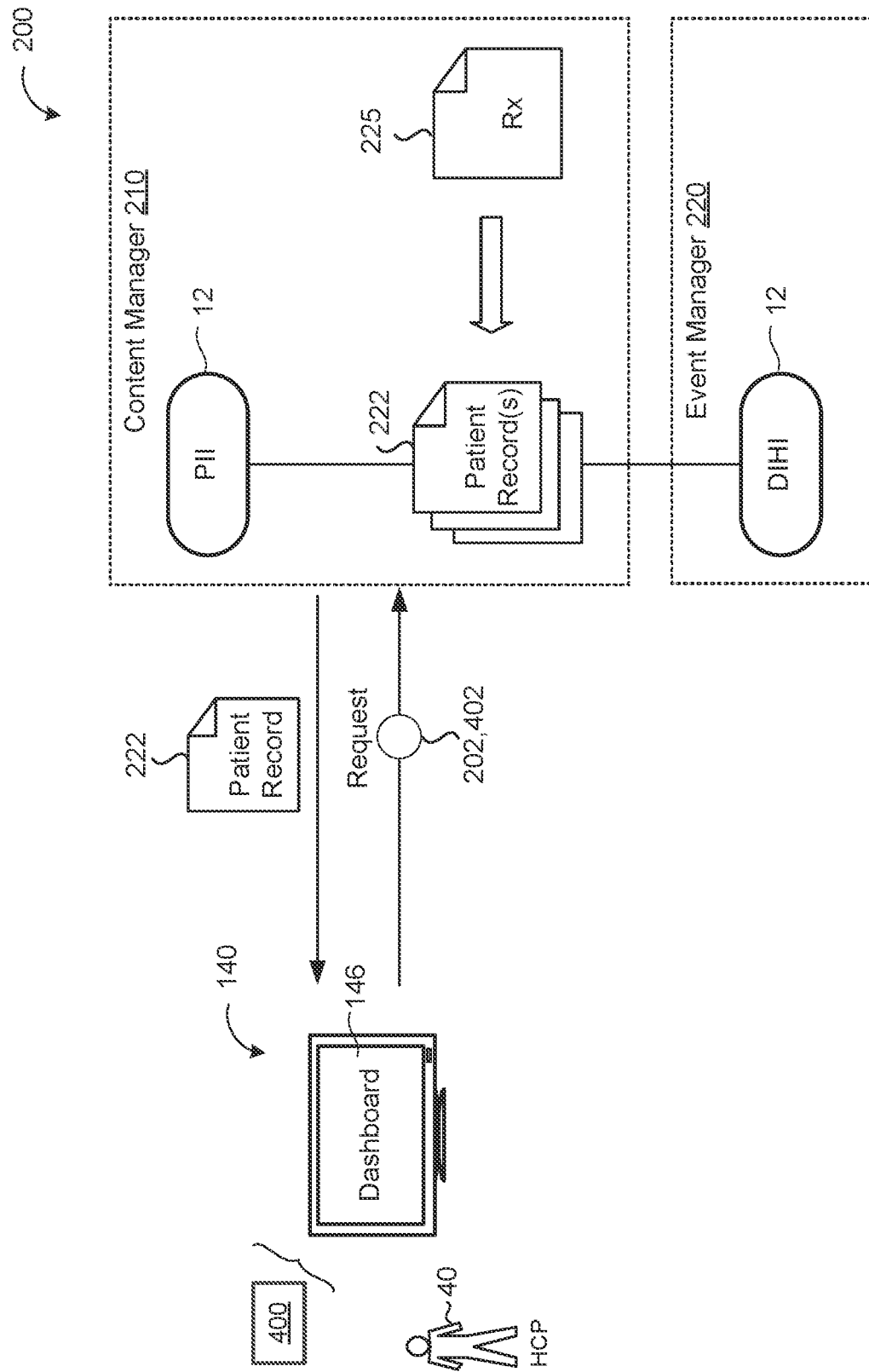
FIG. 2A is a schematic view showing a healthcare professional (HCP) system requesting and retrieving a patient record.

Referring to FIG. 2A, the HCP system 140 may execute the HCP application 400 to request a patient record 222 for a patient 10 under the supervision of the HCP 40 and prescribed a digital therapy prescription 225 by the HCP 40. In the example shown, the HCP system 140 sends a patient record request 202 over the network 20 to the content manager 210 of the backend service 200. The patient record request 202 may identify the patient 10 associated with the requested patient record 222 by including an authentication token 402 indicating that the HCP 40 is authorized to obtain the patient record 222. The authentication token 402 may further identify the patient 10 and/or define a scope for the patient data 12 to be included in the patient record 222.

The patient data 12 associated with the patient 10 may be anonymized when stored by the backend service 200 to protect the privacy of the patient 10. For instance, the event manager 220 may only perform analytics on de-identified health information (DIHI) that includes patient health information which has been separated from the patient identifying information. However, since the HCP 40 needs to view the patient record 222, the content manager 210 is responsible for re-identifying the DIHI from the event manager 220 so that patient record 222 links the patient identifying information to the patient health information. The patient record 222 may further include the digital therapy prescription 225. The content manager 210 may then encrypt the patient record 222 and transmit the patient record 222 over the network 10 to the HCP system 140 via secure communication protocols (e.g., HTTPS or TLS).

In the example shown, the HCP system 140 executing the HCP application 400 may decrypt the patent record 222 and display the patient record 222 on a dashboard displayed on the display 146. The dashboard may display multiple patient records 222 for patients 12 under the supervision of the HCP 40 and prescribed corresponding digital therapy prescriptions 225. The application 400 may cause the dashboard to visually and/or audibly notify the HCP 40 the patient record 222 reveals events satisfying certain criteria. For instance, the application 400 may notify the HCP 40 when a given patient 10 fails a drug screen, reports substance use, or fails to complete a learning module 120a by a defined date.

Figure 2B:
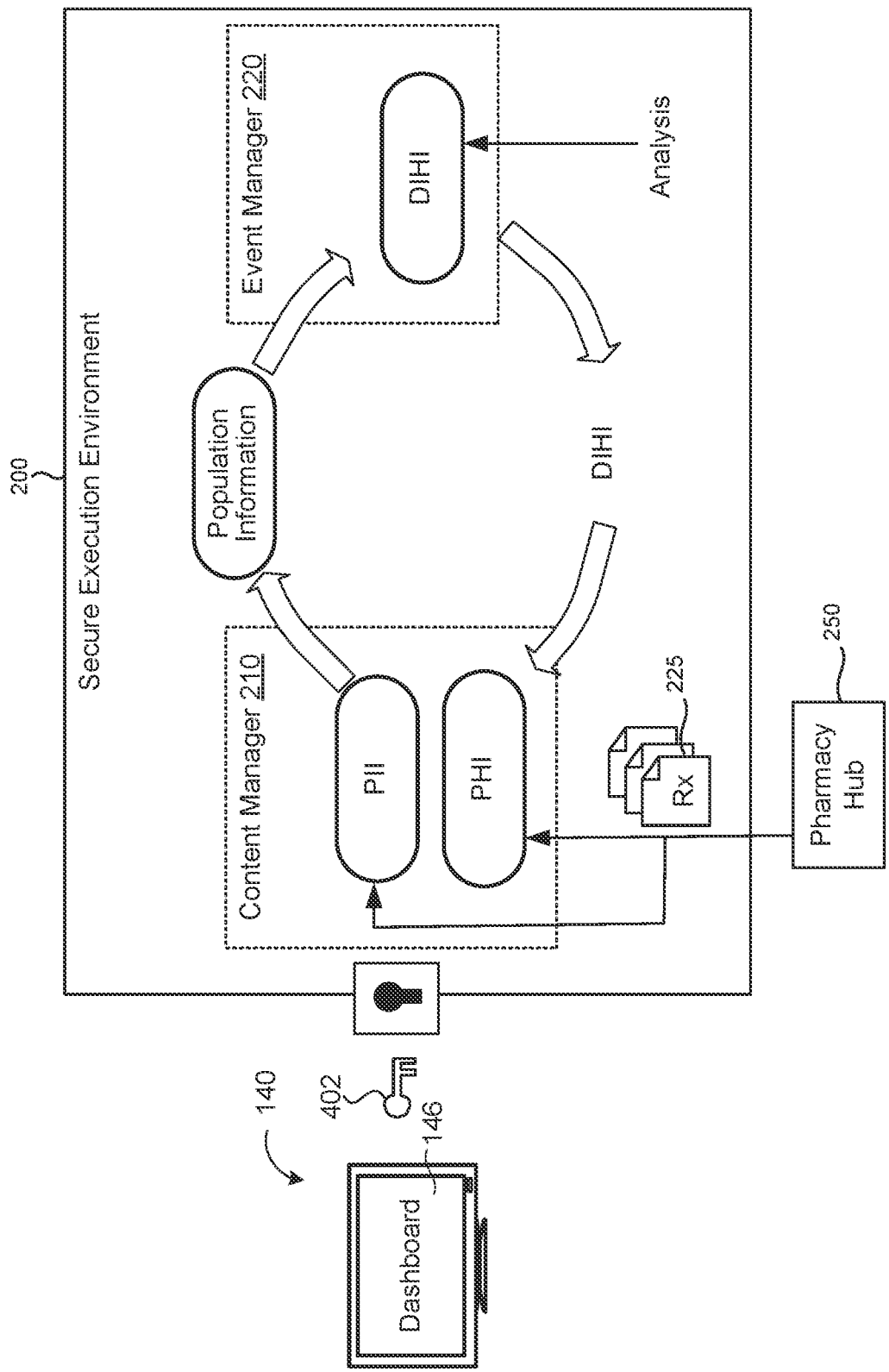
FIG. 2B is a schematic view showing a content manager and an event manager executing in a secure execution environment of a backend service cooperating to analyze de-identified health information and re-identifying the de-identified health information responsive to requests from authorized and authenticated HCPs.

FIG. 2B shows the content manager 210 and the event manager 220 of the backend service 200 running in a secure execution environment. The content manager 210 may separate the PII from the PHI of the patient data 12 to provide DIHI to the event manager 220 for an entire patient population. The event manager 220 may then perform analytics on the DIHI so that patient's identity cannot be linked to the health information. The secure execution environment 200 secures the patient data 12 event from personal employed by the entity providing the backend service 200. In fact, the secure execution environment prevents any entity or individual, aside from the authorized HCP 40 and the patient 10, from freely inspecting any of the contents within the secure execution environment. In some implementations, a select individual may be authorized to perform a "break-glass" event to gain access to the secure execution environment in the event of a system failure or emergency maintenance.

A pharmacy hub 250 may input prescriptions 225 to the backend service 200 via the content manager 210. The pharmacy hub 250 may include a prescription service that fills prescriptions for patients 10. The prescriptions 225 are associated with patient data 12 that includes both PHI information and PII identifying the patient 10 associated with the PHI. Thus, the content manager 210 may de-identify the patient data 12 so that only DIHI is provided and analyzed by the event manager 220 so that each patient's identity is anonymized. In order for the HCP system 140 to retrieve patient data 12 (e.g., patient records 222) that include the PII, the HCP system 140 must provide a corresponding authentication token 402 that the content manager 210 must validate. In some examples, the pharmacy hub 250 generates the digital therapy prescription 225 and provides it to the patient 10 when the patient 10 presents the required access code 302.

Figure 3:
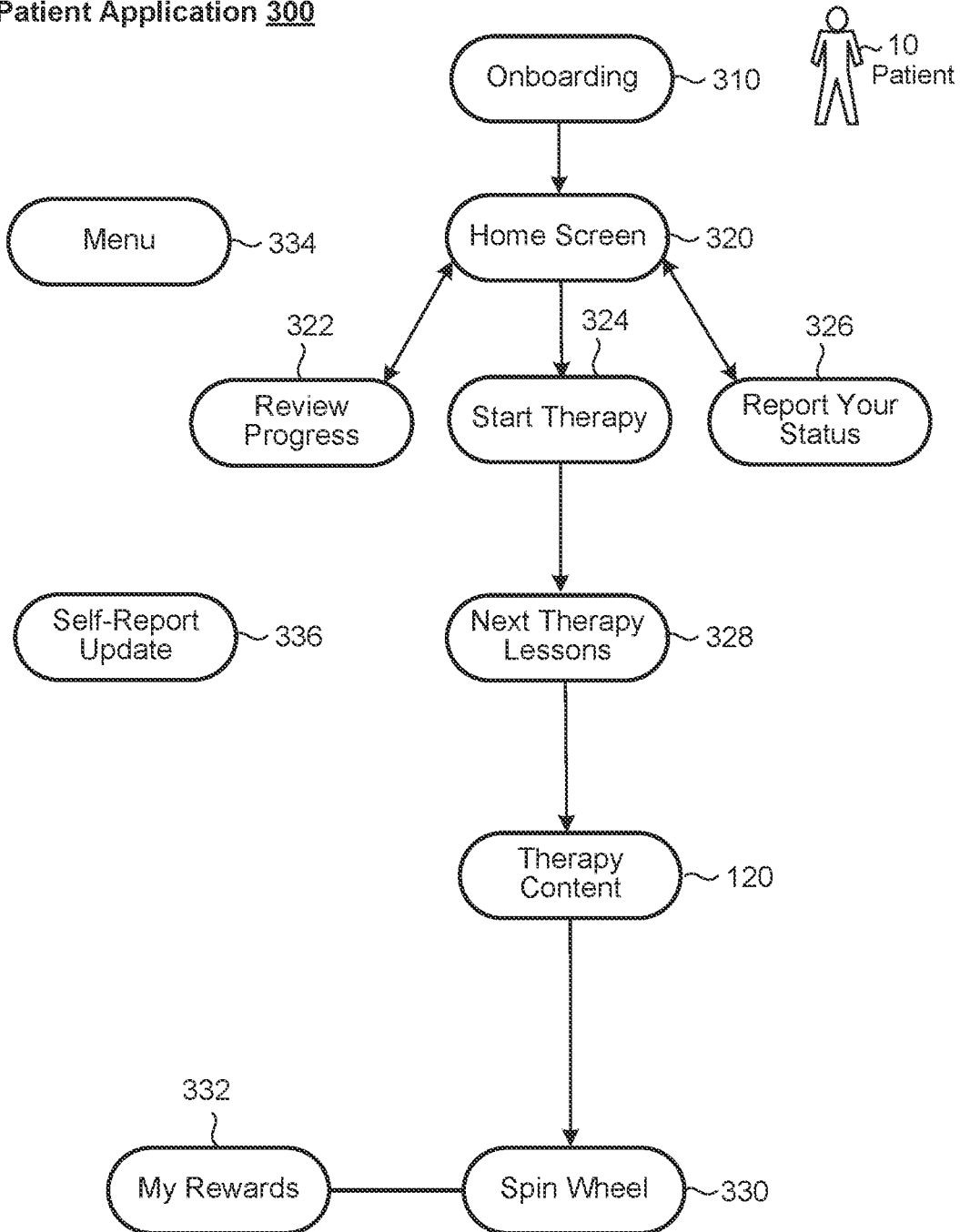
FIG. 3 is a schematic view of example components of a patient application of the system of FIG. 1 executing on a patient device.

FIG. 3 is a schematic view of example components of the patient application 300 executing on the patient device 110. The patient application 300 may include application logic, an underlying mobile Software Development Kit (SDK) that is responsible for client-server communication and a content management engine that is responsible for asynchronously loading content 120 from the backend service 200. The application 300 may capture and communicate real-time events to the backend service 200 for storage as immutable data stored on the storage resources 156 by the event manager 220. The mobile SDK may manage authentication, content management, and secure management.

Communication with the backend service 220 include three exemplary categories: content setup and management; patient identity and authentication services; and patient module use and event tracking. The content management infrastructure may dynamically manage loadable therapy content 120 for presentation to the patient 10. This content may be global, i.e., consistent across patients 10 and may include, for example, learning module 120a content, proficiency tests 120b, graphics and/or audio and/or video content 120c, application guidelines 120d for using the application 300, and assessment questions 120e and answers. The therapy content 120 may be stored in the content data storage 156b of the storage system 156 in the cloud computing environment 150. The patient identity and authentication services managed by the mobile SDK may manage login and in-memory storage of an authorization token used for all requests to the backend services. The authorization token may include the access code 302 and/or the authentication token 402. The event tracking service captures use of the learning modules 120a (e.g., frequency and completion) and patient-reported events such as substance use, cravings, and/or craving triggers that may be automatically sent to the event manager 220 when a network connection is available so that a supervising HCP may access these patient events via the HCP application 400 for presentation on the dashboard. Accordingly, the event manager 220 is configured to track events generated by the patient application 300 as well as the HCP application 400. All communications between the backend service 200 and the patient application 300 may be encrypted and transmitted over secure protocols such as HTTPS or TLS.

In some examples, the content manager 210 may provide therapy content 120 to the patient device 110 and the patient application 300 may install or locally store the therapy content 120 so that it is available ahead of time when the patient 10 loads a desired learning module 120a through the patient application 300. For instance, the application 300 may download and/or load a next available therapy lesson in a given learning module 120a after a patient completes a current therapy lesson while logged into the application 300. This can improve latency and patient experience so that the patient can quickly move on to a next therapy lesson without having to take steps to select and wait for the selected therapy lesson to download and/or load. The application 300 may further facilitate streaming of video/audio content 120c from the content data store 156b. As used herein, the learning modules 120a may present the patient with a core learning section that includes multiple lessons that the patient 10 must follow and complete in order one lesson at a time. The lessons may educate the patient 10 on the disease or disorder the patient is seeking treatment for as well as provide specific guidelines for the patient 10 to follow to treat the underlying disease/disorder. The therapy lessons may correspond a cognitive behavioral therapy learning portion of the digital therapy prescription for treating the underlying disease/disorder. The learning modules 120a may further include a keep learning section that unlocks after each lesson in the core lection section is complete. The keep learning section may include lessons that may be accessed in any order. The patient 10 may be required to successfully answer assessment questions 120e or pass proficiency tests 120b before moving on to a next lesson. All interaction by the patient 10 with these learning modules 120a (e.g., progress or completion status) and therapy content 120 may be reported by the application 300 to the event manager 220 for storage as immutable event data that may be logged to the patient record 222 and accessed by the supervising HCP via the HCP application 400.

Still referring to FIG. 3, the application 300 provides initial onboarding 310 to register a patient 10 by inputting a valid access code 302 (via a registration request sent to the content manager 210). The patient 10, at his or her email address, may receive a verification email indicating that the patient 10 has been enrolled by the HCP 40 to register the patient application 300 for accessing the digital therapy prescription 225, and the verification email may include the access code 302 that the patient 10 must enter to verify enrollment and complete the registration. The access code 302 may be provided with the digital therapy prescription to indicate that the patient 10 is authorized to access the digital therapy prescription 225 prescribed to the patient 10. The access code 302 may only be valid for a predetermined period of time. The patient may provide a user name or email with the access code 302 to complete the registration, and then may setup a password for logging into the application 300. As used herein, logging into the patient application 300 refers to the application 300 presenting a home screen 320 to permit the patient 10 to navigate the application 300 to initiate therapy/treatment, review status of completed or in progress learning modules 120a, and any previous event history associated with the patient's use of the application 300 and reports of compliance by the supervising HCP 40. Logging into the application 300 may include establishing a connection with the backend service 200 when a connection to the network 20 is available. The password may be stored in an electronic keychain so that the patient 10 does not have to input a password from the same device 110 each time the patient 10 wants to launch the application 300. The onboarding 310 may further require the patient 10 to review and accept a terms of service, consent to rewards, and review a user guide for using the application 300 before registering the patient 10 with the application 300. The digital therapy prescription 225 prescribed to the patient 10 may start upon successful registration and log in to the patient application 300. The prescription may include 225 a validity period (e.g., 90 days) that commences upon successful registration and expires at the end of the validity period.

After the patient 10 is registered, the patient 10 may login to the patient application 300 by inputting appropriate credentials (e.g., username/email and password) in order to present the home screen 320 of the application 300. From the home screen 320, the patient 10 may navigate to a Review Progress screen 322, Start Therapy screen 324, or a Report Your Status screen 326. The Review Progress screen 322 allows the patient 10 to access charts directed toward cravings and/or triggers that cause the patient 10 to crave using a substance. The Report Your Status screen 326 allows the patient to track use, craving intensity, and/or trigger intensity associated with a particular substance. The Start Therapy screen 324 directs the patient to a Next Therapy Lessons screen 328 indicating a lesson from a learning module 120a that is currently in progress that the patient 10 must complete or a next lesson from the learning module 120a that the patient 10 is directed to access and complete. Accordingly, the Next Therapy Lessons screen 328 may include the ordered list of core lessons that the patient must complete one at a time before advancing to a next lesson, or may include the keep learning lessons that unlock after completing the core lessons and that may be completed in any order. Once a lesson from a learning module 120a is accessed via the Next Therapy Lessons screen 328, the patient application 300 may retrieve or load therapy content 120 associated with the lesson. The therapy content 120 may include audio/video content that supplements the lessons of the learning module 120a. Optionally, the application 300 may load proficiency tests and/or assessment questions associated with the lesson that the patient must pass/answer in order to complete the lesson. The application 300 may further present a Spin Wheel screen 330 that graphically displays a virtual prize wheel that the patient 10 may spin upon successful completion of a lesson. The virtual prize wheel may include numerous slots each representing a reward that the patient 10 can redeem when the wheel lands on that slot. The application 300 may present a My Rewards screen 332 that provides a list of rewards obtained by the patient 10.

The application 300 may present a Menu button 334 that may be available for selection when the patient 10 is logged in to navigate to any of the aforementioned screens and/or review the user guide, terms of service, reward consent, privacy policy/settings, or other information related to the application 300 that the patient 10 may want to view/access. The patient 10 may further select a Self-Report Update button 336 to report substance use events each indicating the substance used by the patient, the date/time of use, and an urge intensity the patient 10 felt before using the substance. The application 300 may report these events to the event manager 220 when a network connection is available. When a network connection is not available, the application 300 may timestamp the events and store them locally in a cache/queue until the network connection is available.

Figure 4:
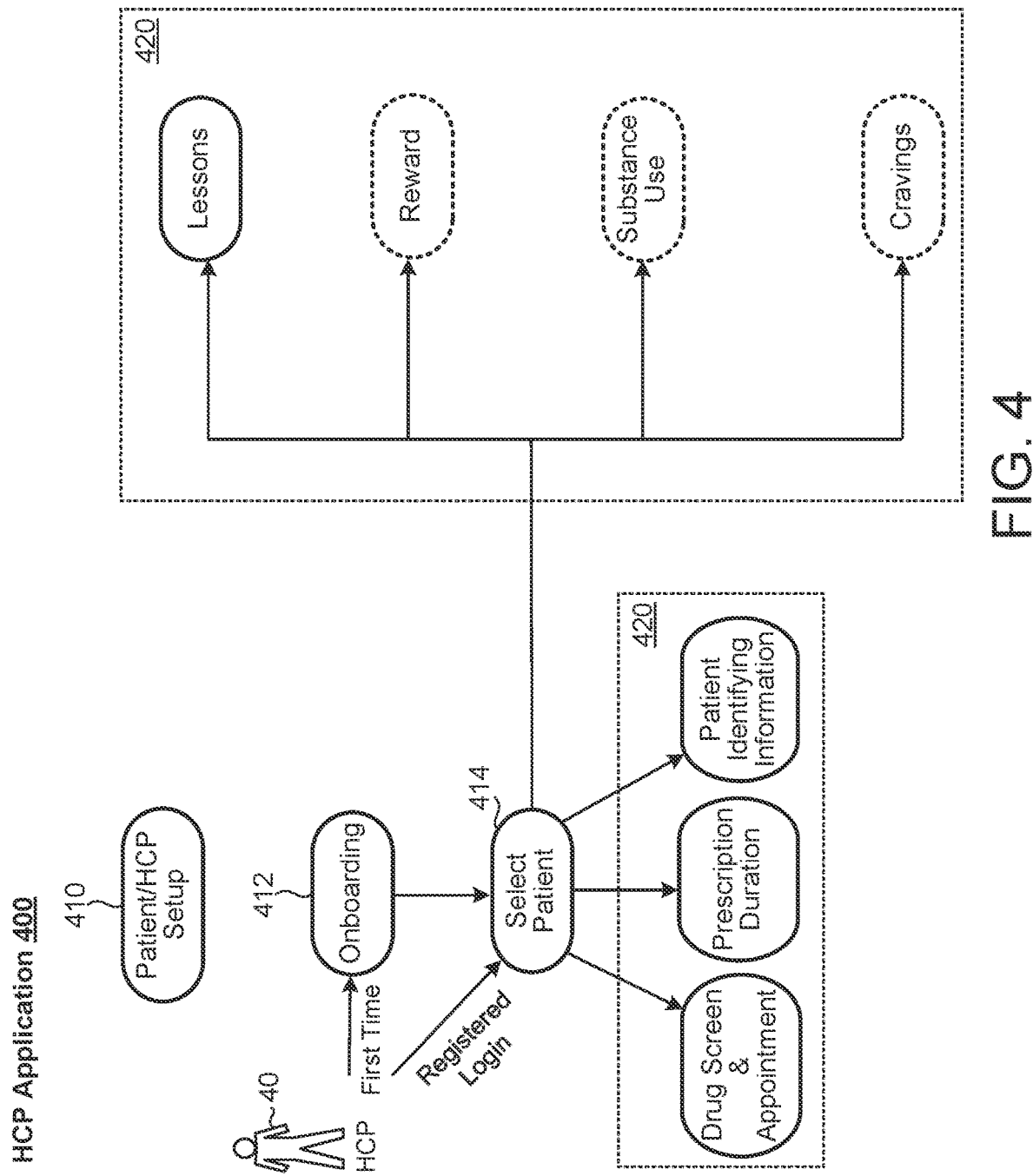
FIG. 4 is a schematic view of example components of an HCP application of the system of FIG. 1 executing on an HCP device.

FIG. 4 is a schematic view of example components of the HCP application 400 executing on the data processing hardware 142 of the HCP system 140 or accessible by the data processing hardware 142 as a web-based application. The HCP application 400 requires that each user of the HCP application 400 be explicitly assigned a clinician role by an HCP administrator. Accordingly, the HCP 40 may include multiple 'clinicians' that may have permission and appropriate credentials to log into the HCP application and access patient-related data. In some examples, the HCP 40 may include clinicians explicitly associated with patients 10 in a context of a single clinic program and include provisions such as a many-to-many relationship where a single clinician can supervise many patients and a single patient can be under the supervision of multiple clinicians. As used herein, when a patient 10 is under the supervision of the HCP 40 (or clinician), the HCP 40 (or clinician) is understood to be authorized to be able retrieve data (e.g., patient records 222, time series patient event data, etc.) stored by the backend service 200 on the storage resources 156 by presenting appropriate credentials and a valid authentication token 402. However, a given clinician only has visibility to patient-related data belonging to patients for whom a patient relationship has been established, i.e., for patients under the supervision of the clinician.

An administrator (e.g., HCP 40) of the HCP system 140 may use an API to communicate with the content manager 210 to set up one or more clinicians for a given clinic and establish HCP-patient relationships. The administrator may initially receive an account verification email from the backend service 200. By accessing a Patient/HCP Setup interface 410 provided by the HCP application 400, the administrator may add clinicians by providing corresponding HCP data 42 for each clinician that may include, without limitation, first and last name of the clinician, birth date, email address, and group/name of the HCP 40 the clinician is associated with. The content manager 210 then enrolls the clinician and sends an email to the clinician that may include a link that directs the clinician to verify their account and to create a password for logging into the HCP application 400. As shown in FIG. 4, the selection of the link in the email may cause the HCP application 400 to launch and present an onboarding screen 412 that allows the clinician to register with the HCP application 400 by creating the password. Thereafter, the clinician may log into the HCP application 400 using his or her email and the password. Similarly, the administrator may access the Patient/HCP Setup interface 410 to add new patients by providing corresponding patient data 12 for each patient 10 that may include, without limitation, the HCP 40 (e.g., clinic/hospital group) the patient 10 being treated by, first and last name of the patient, birth date, and email address. This add new patient input is effective to enroll a new patient 10 to register with the patient application 300 for access to the digital therapy prescription to treat the underlying disease/disorder. The content manager 210 may then send a verification email to the patient's 10 provided email address, whereby the verification email includes the access code 302 the patient 10 must input to complete the registration with the patient application 300, as described above with reference to the onboarding 310 of FIG. 3.

With continued reference to FIG. 4, a registered clinician 40 provides his or her email address (or a unique user name or account number) and password to log in to the application 400 and the application 400 presents a Select Patient screen 414 that allows the clinician to search or view all patients 10 the clinician has a relationship with. The clinician may select individual patients to view their patient records 222. For instance, selection of the patient 10 in the dashboard may cause the application 400 to transmit the patient record request 202 (FIG. 2A) to the content manager 210 to instruct the content manager 210 to retrieve the requested patient record 222 from the storage resources. The HCP application 400 may present a patient dashboard 420 once the patient record 222 is received from the content manager 210. The application 400 may extract, from the patient record 222 and for display in the patient dashboard 420 presented on display 146), patient data 12 (e.g., patient identifying information such as name, date of birth, age, gender and/or patient health information such as diagnosis, medications, life events, etc.), prescription duration indicating a status (e.g., days remaining from an initial number of days) of the digital therapy prescription prescribed to the patient, and Drug Screen & Appointment data indicating whether or not the clinician 40 saw the patient 10 on the current day and whether or not the patient 10 had a drug screen on the current day and the result of that drug screen. The prescription duration may include text and/or graphics indicating the status of the prescription 225. The HCP application 400 may generate a notification to alert the HCP 40 when the prescription 225 expires and/or some period of time (e.g., one day) before the prescription 225 expires.

The patient dashboard 420 further presents selectable tabs for Lessons, Rewards, Substance Use, and Cravings related to the selected patient 420. In the example shown, the Lessons tab includes solid lines indicating that the Lessons tab is selected and the patient dashboard 420 is currently displaying data (e.g., plot/chart) of the patient's status in completing learning modules 120a and lessons associated therewith as well as a duration the patient 10 spent on lessons for each day over a selectable period of time. The Rewards, Substance Use, and Cravings tabs include dashed lines indicating that the tabs are not selected and the patient dashboard 420 is not presenting data associated with those tabs.

Selecting the rewards tab causes the HCP application 400 to display a list of all rewards earned by the patient 10 on the patient dashboard 420. Each reward may indicate a reward type, a date of the reward, and a reward amount. The reward type can include a clean screen reward each time the patient 10 passes a scheduled drug screen and a lesson completion reward when the patient 10 successfully completes a lesson. The patient dashboard 420 may further displays a total number of rewards earned by the patient 10, a total reward amount that sums up the value of each of the rewards, and outstanding rewards that have not been fulfilled but are otherwise available for the patient 10 (e.g., upon completion of a lesson in a learning module or passing a drug screen).

Selecting the Substance Use tab causes the HCP application 400 to populate substance use data from the patient record 222 and display the populated substance use data for the patient on the patient dashboard 420. Here, the substance use data presented on the patient dashboard 420 may indicate a total number of days the patient 10 used the substance, days in a current month the patient 10 used the substance, and/or a calendar indicating results of drug screens, scheduled appointments attended/missed by the patient 10, and patient reported use/non-use of the substance.

Selecting the Cravings tab causes the HCP application 400 to populate cravings data reported by the patient 10 during a cravings assessment and logged in the patient record 222 for display on the patient dashboard 420. Here, the cravings data presented on the patient dashboard 420 may include average intensity and number of cravings during a current week. The patient dashboard 420 may further display a craving intensity scatter data chart including date range input fields that may be set by the HCP 40, a data range selector, and a "used" indicator that corresponds to a graphic indicating that the patient 10 used a substance associated with the cravings. The patient dashboard 420 may further display a bubble chart based on the craving data.

FIG. 5 provides an example diagram showing interaction between the patient application 300, the HCP application 400, the content manager 210, and the event manager 220 of the system 100 of FIG. 1. FIG. 5 may be described with reference to FIGS. 1-4. As set forth above, the event manager 220 is configured to act as a sink for receiving patient-generated event data 304 and HCP-generated event data 404. The applications 300, 400 may automatically report corresponding event data 304, 404 to the event manager 220 during periods of available network connectivity. When network connectivity is not available, the applications 300, 400 may locally queue the event data 304, 404 in memory hardware 114, 144 and then flush the event data 304, 404 once a network connection with the event manager 220 is established. The event manager 220 may store the patient-generated event data 304 as immutable time series event data including a time stamp of when the event occurred. The patient-generated event data 304 for each patient 10 may be stored in the corresponding patient record 222 within the patient/HCP data storage 156a. The patient-generated event data 304 may include, without limitation, craving and use patient initiated assessment; DFU step completed; DFU completed; lesson assessment results; lesson completed; lesson used; reward acknowledged, patient self-report updates; terms of service accepted, application 300 opened, application 300 resume, application 300 suspended, logged in, logged out, patient usage report, prescription notification displayed, and prescription notification confirmed.

The event manager 220 may similarly store the HCP-generated event data 404 as immutable time series event data including a time stamp of when the event occurred. Here, the HCP-generated event data 404 for each HCP 40 (or individual clinicians of a same HCP) may be stored in the corresponding HCP record 224 within the patient/HCP data storage 156a. The HCP-generated event data 404 may include, without limitation, terms of service acceptance, application 300 opened, application 300 resume, application 300 suspended, logged in, and logged out.

The content manager 210 may further store patient data 12 for each patient 10 in the corresponding patient record 222 within the patient/HCP data storage 156a. The patient data 12 may include, without limitation, general patient information such as name, age, birth date, gender, height/weight, medications; the HCPs treating the patient 10; the access code 302 associated with the patient 10 for registering with the patient application 300 and commencing the digital therapy prescription 225; and the authentication token 402 associated with the patient 10. The patient application 300 may provide some of the patient data 12 to the content manager 210 during initial onboarding when the patient registers the application. The HCP application 400 may provide other portions of the patient data 12 to the content manager 210 when the supervising HCP 40 is enrolling the patient 10 to use the patient application 300 as a component of the digital therapy prescription 225 prescribed to the patient 10.

The content manager 210 may similarly store HCP data 42 for each HCP 40 in the corresponding HCP record 224 within the patient/HCP data storage 156a. The HCP data 42 may include, without limitation, general HCP information such as name, birthdate, email address, practice group or clinic, a list of patients 10 the HCP 40 is treating/supervising, and authentication tokens 402 each patient 10 the HCP 40 is supervising and having an active therapy prescription 225.

The patient and event data 12, 304 within each patient's record 222 is de-identified so that the identity of the patient 10 is anonymized while stored in the data storage 156a and/or when the event manager 220 performs analytics on the data 12, 304. However, an HCP 40 supervising the patient 10 may use the HCP application 400 to send a patient record request 202 requesting the content manager 210 to retrieve the patient record 222 and provide the patient record 222 to the requesting HCP 40 when the HCP 40 provides a valid authentication token 402. Here, the authentication token 402 may be specific to the patient 10 and allows the content manager 210 to identify the correct patient record 222. For instance, the authentication token 402 and the patient record 222 may include matching cryptographic hashes. The patient 10 may similarly use the patient application 300 to query/request the content manager 210 to retrieve and provide the patient record 222 to the patient 10 when the patient 10 provides the authentication token 402 or some other valid credentials. As set forth above, the content manager 210 encrypts the patient record 222 before transmitting to the HCP system 140 or patient device 110 and the corresponding application 300, 400 decrypts the patient record 222 to view and present the contents thereof on the corresponding display 116, 146. The HCP 40 may similarly query the content manager 210 to retrieve immutable time series event data stored by the event manager 220 and associated with each of one or more patients under the supervision of the HCP 40. For instance, the HCP 40 may use the HCP application 400 to make the patient record request 202 by including the appropriate authentication token(s) 402.

With continued reference to FIG. 5, the patient application 300 may send a content request for therapy content 120 when the patient 10 selects a therapy lesson in the Next Therapy Lessons screen 328 (FIG. 3). The application 300 may automatically send the request and the therapy content 120 retrieved may include any therapy content associated with the selected therapy lesson. While FIG. 5 shows the patient application 300 directly requesting the content data storage 156a, the request may be communicated to the content manager 210 and the content manager may retrieve the appropriate therapy content 120 from the content data storage 156b and transmit the retrieved therapy content 120 to the patient application 300.

Figure 6:
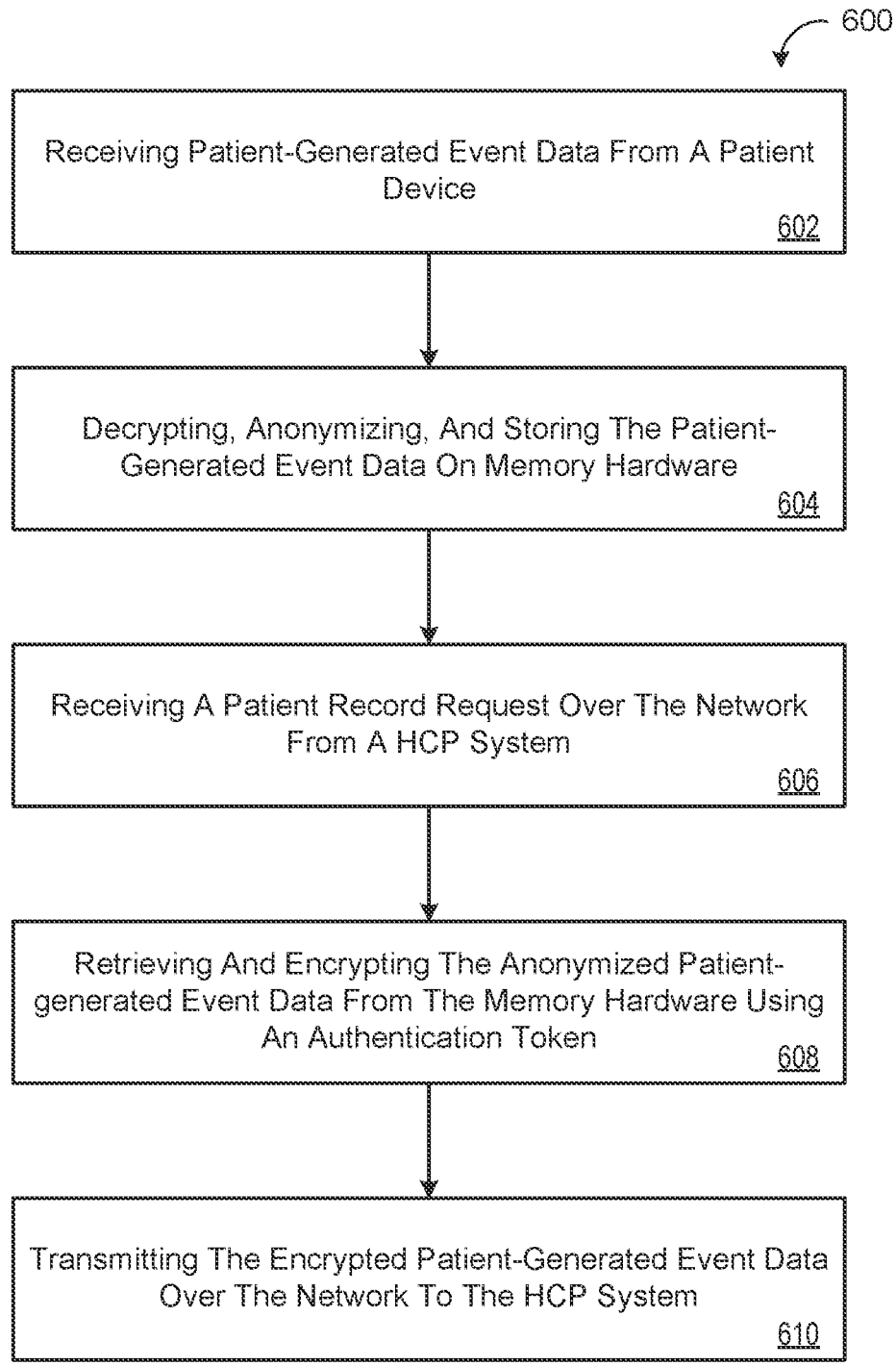
FIG. 6 is a flowchart of an example arrangement of operations for a method of storing and retrieving patient-generated event data on a distributed system.

FIG. 6 is a flowchart of an example arrangement of operations for a method 600 of storing and retrieving patient-generated event data 304. The content manager 210 and/or the event manager 220 of the data processing hardware 154 of the backend service 200 may execute the operations for the method 600 by executing instructions stored on the memory hardware 156. At operation 602, the method 600 includes receiving, at the data processing hardware 154, the patient-generated event data 304 over a network 20 from a patient device 110. The patient device 110 is associated with a patient 10 having an active digital therapy prescription 225 prescribed by a supervising healthcare professional (HCP) 40 for treating an underlying disease or disorder. The patient-generated event data 304 is encrypted by the patient device 110 and includes at least one timestamped event related to the active digital therapy prescription 225. At operation 604, in response to receiving the patient-generated event data 304, the method 600 includes: decrypting, by the data processing hardware 154, the patient-generated event data 304; anonymizing, by the data processing hardware 154, the patient-generated event data 304 by removing any patient identifying information from the patient-generated event data 304; and storing, by the data processing hardware 154, the anonymized patient-generated event data 304 on the memory hardware 156.

At operation 606, the method 600 further includes receiving, at the data processing hardware 154, a patient record request 202 over the network 20 from a HCP system 140 associated with the HCP 40 supervising the patient 10. The patient record request 202 requests the patient-generated data 304 and includes an authentication token 402. At operation 608, in response to receiving the patient record request 202, the method 600 also includes retrieving, by the data processing hardware 154, the anonymized patient-generated event data 304 from the memory hardware 156 using the authentication token 402 and encrypting, by the data processing hardware 154, the patient-generated event data 304. At operation 610, the method 600 includes transmitting, by the data processing hardware 154, the encrypted patient-generated event data 304 over the network 20 to the HCP system 140. The encrypted patient-generated event data 304 when received by the HCP system 140 causes the HCP system 140 to decrypt the patient-generated event data 304 and present the patient-generated event data 304 in a patient dashboard screen of a display 146 of the HCP system 140.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Figure 7:
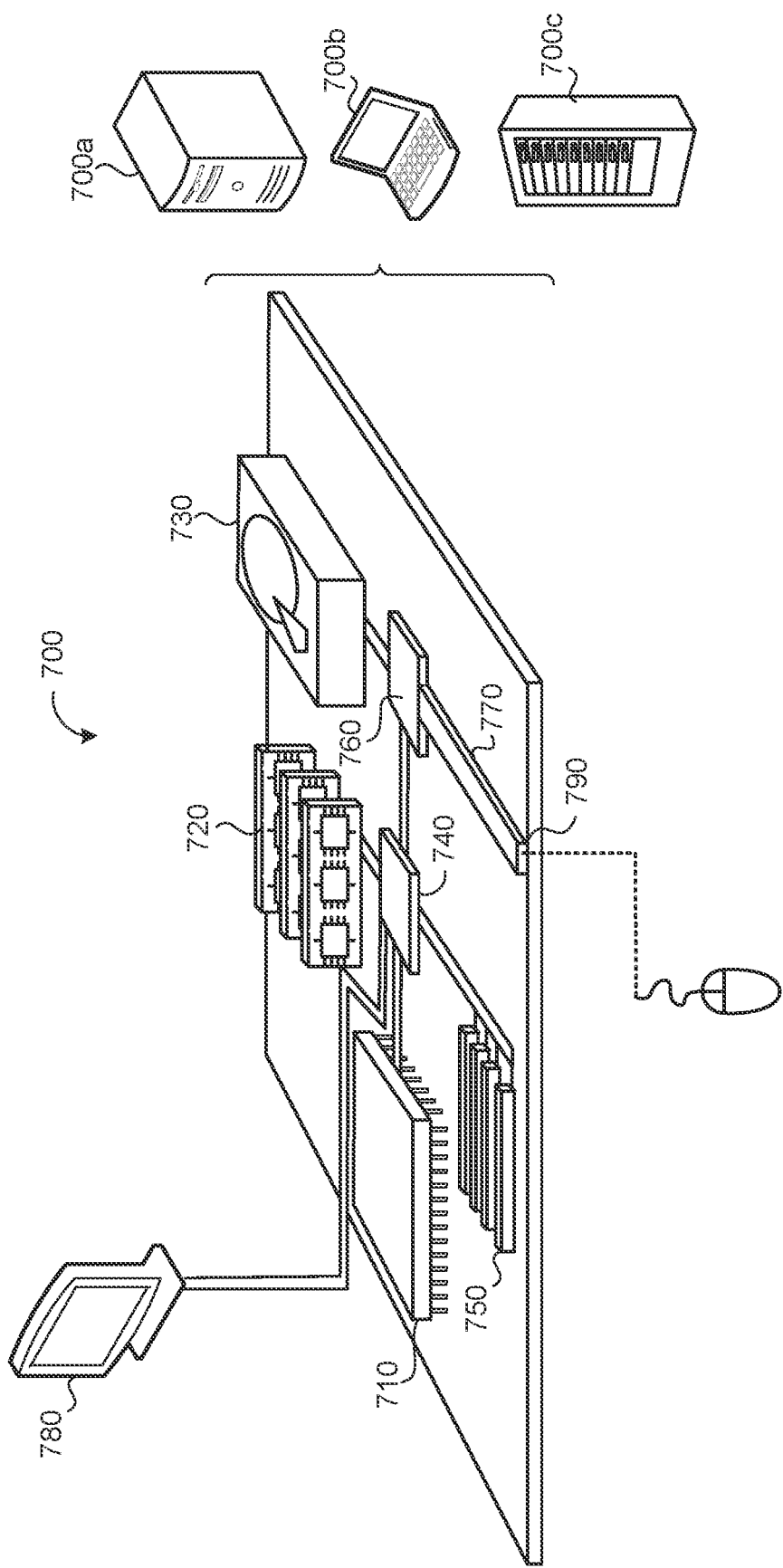
FIG. 7 is a schematic view of an example computing device.

FIG. 7 is schematic view of an example computing device 700 that may be used to implement the systems and methods described in this document. The computing device 700 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 700 includes a processor 710, memory 720, a storage device 730, a high-speed interface/controller 740 connecting to the memory 720 and high-speed expansion ports 750, and a low speed interface/controller 760 connecting to a low speed bus 770 and a storage device 730. Each of the components 710, 720, 730, 740, 750, and 760, are interconnected using various busses, and may be mounted on a common motherboard or in other manners as appropriate. The processor 710 can process instructions for execution within the computing device 700, including instructions stored in the memory 720 or on the storage device 730 to display graphical information for a graphical user interface (GUI) on an external input/output device, such as display 780 coupled to high speed interface 740. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 720 stores information non-transitorily within the computing device 700. The memory 720 may be a computer-readable medium, a volatile memory unit(s), or non-volatile memory unit(s). The non-transitory memory 720 may be physical devices used to store programs (e.g., sequences of instructions) or data (e.g., program state information) on a temporary or permanent basis for use by the computing device 700. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 730 is capable of providing mass storage for the computing device 700. In some implementations, the storage device 730 is a computer-readable medium. In various different implementations, the storage device 730 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 720, the storage device 730, or memory on processor 710.

The high speed controller 740 manages bandwidth-intensive operations for the computing device 700, while the low speed controller 760 manages lower bandwidth-intensive operations. Such allocation of duties is exemplary only. In some implementations, the high-speed controller 740 is coupled to the memory 720, the display 780 (e.g., through a graphics processor or accelerator), and to the high-speed expansion ports 750, which may accept various expansion cards (not shown). In some implementations, the low-speed controller 760 is coupled to the storage device 730 and a low-speed expansion port 790. The low-speed expansion port 790, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 700a or multiple times in a group of such servers 700a, as a laptop computer 700b, or as part of a rack server system 700c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method comprising:
receiving, at data processing hardware, patient-generated event data from a patient device associated with a patient being treated with a digital therapeutic, the patient-generated event data including at least one timestamped event related to the digital therapeutic, the digital therapeutic including interactive digital therapy content for treating an underlying disease or disorder, the patient-generated event data encrypted by the patient device;
decrypting and anonymizing, by the data processing hardware, the patient-generated event data;
receiving, at the data processing hardware, a patient record request from a healthcare professional (HCP) system associated with a HCP supervising the patient, wherein the patient record request requests the patient-generated event data;
retrieving, by the data processing hardware, the anonymized patient-generated event data;
encrypting, by the data processing hardware, the patient-generated event data;
transmitting, by the data processing hardware, the encrypted patient-generated event data to the HCP system, the encrypted patient-generated event data when received by the HCP system causing the HCP system to decrypt the patient-generated event data; and
wherein the encrypted patient-generated event data received by the HCP system causes the HCP system to present a notification related to the at least one timestamped event on the HCP system, the notification including one of a visual alert or an audible alert.

2. The method of claim 1, wherein the patient-generated event data is anonymized by the data processing hardware removing any patient identifying information from the patient-generated event data.

3. The method of claim 1, wherein the visual alert is displayed on a screen of the patient device or the audible alert is output by speakers of the patient device.

4. The method of claim 1, further comprising, prior to receiving the patient-generated event data:

receiving, at the data processing hardware, a registration request from the patient device, the registration request comprising an access code and requesting the patient to register the patient device with a patient application for accessing the digital therapeutic;
determining, by the data processing hardware, whether the access code is valid; and
when the access code is valid, prompting, by the data processing hardware, the patient to register the patient device with the patient application.

5. The method of claim 4, further comprising:
receiving, at the data processing hardware, an add patient input from the HCP system, the add patient input enrolling the patient for access to the digital therapeutic for treating the underlying disease or disorder, the add patient input comprising an email address of the patient; and
transmitting an enrollment verification email from the data processing hardware to the patient device using the email address of the patient, the enrollment verification email comprising the access code and instructing the patient to input the access code to transmit the registration request.

6. The method of claim 1, further comprising in response to receiving the patient-generated event data, storing, by the data processing hardware, the anonymized patient-generated event data on cloud storage resources in communication with the data processing hardware.

7. The method of claim 6, wherein the anonymized patient-generated event data is retrieved from the cloud storage resources using an authentication token included with the patient record request.

8. The method of claim 7, wherein retrieving the anonymized patient-generated event data from the cloud storage resources using the authentication token comprises identifying the anonymized patient-generated event data by matching cryptographic hashes associated with the authentication token and the anonymized patient-generated event data.

9. The method of claim 1, further comprising:
receiving, at the data processing hardware, a therapy content request from the patient device, the therapy content request requesting the therapy content related to the digital therapeutic of the patient;
retrieving, by the data processing hardware, the requested therapy content related to the digital therapeutic of the patient from memory hardware in communication with the data processing hardware; and
transmitting, by the data processing hardware, the therapy content to the patient device, the therapy content when received by the patient device causing a patient application executing on the patient device to visually and/or audibly output the therapy content from the patient device.

10. The method of claim 9, wherein the therapy content comprises a learning module that includes one or more therapy lessons the patient has to complete during a duration of the digital therapeutic, the one or more therapy lessons corresponding to a cognitive behavioral therapy learning portion of the digital therapeutic for treating the underlying disease or disorder.

11. A system comprising:
data processing hardware;
memory hardware in communication with the data processing hardware and storing instructions that when executed by the data processing hardware cause the data processing hardware to perform operations comprising:

receiving patient-generated event data from a patient device associated with a patient being treated with a digital therapeutic, the patient-generated event data including at least one timestamped event related to the digital therapeutic, the digital therapeutic including interactive digital therapy content for treating an underlying disease or disorder, the patient-generated event data encrypted by the patient device;

decrypting and anonymizing the patient-generated event data;

receiving a patient record request from a healthcare professional (HCP) system associated with a HCP supervising the patient, wherein the patient record request requests the patient-generated event data;

retrieving the anonymized patient-generated event data;

encrypting the patient-generated event data;

transmitting the encrypted patient-generated event data to the HCP system, the encrypted patient-generated event data when received by the HCP system causing the HCP system to decrypt the patient-generated event data; and wherein the encrypted patient-generated event data received by the HCP system causes the HCP system to present a notification related to the at least one timestamped event on the HCP system, the notification including one of a visual alert or an audible alert.

12. The system of claim 11, wherein the patient-generated event data is anonymized by the data processing hardware removing any patient identifying information from the patient-generated event data.

13. The system of claim 11, wherein the visual alert is displayed on a screen of the patient device or the audible alert is output by speakers of the patient device.

14. The system of claim 11, wherein the operations further comprise, prior to receiving the patient-generated event data:

receiving a registration request from the patient device, the registration request comprising an access code and requesting the patient to register the patient device with a patient application for accessing the digital therapeutic;

determining whether the access code is valid; and when the access code is valid, prompting the patient to register the patient device with the patient application.

15. The system of claim 14, wherein the operations further comprise:

receiving an add patient input from the HCP system, the add patient input enrolling the patient for access to the digital therapeutic for treating the underlying disease or disorder, the add patient input comprising an email address of the patient; and transmitting an enrollment verification email from the data processing hardware to the patient device using the email address of the patient, the enrollment verification email comprising the access code and instructing the patient to input the access code to transmit the registration request.

16. The system of claim 11, wherein the operations further comprise, in response to receiving the patient-generated event data, storing the anonymized patient-generated event data on cloud storage resources in communication with the data processing hardware.

17. The system of claim 16, wherein the anonymized patient-generated event data is retrieved from the cloud storage resources using an authentication token included with the patient record request.

18. The system of claim 17, wherein retrieving the anonymized patient-generated event data from the cloud storage resources using the authentication token comprises identifying the anonymized patient-generated event data by matching cryptographic hashes associated with the authentication token and the anonymized patient-generated event data.

19. The system of claim 11, wherein the operations further comprise:

receiving a therapy content request from the patient device, the therapy content request requesting the therapy content related to the digital therapeutic of the patient;

retrieving the requested therapy content related to the digital therapeutic of the patient from the memory hardware; and transmitting the therapy content to the patient device, the therapy content when received by the patient device causing a patient application executing on the patient device to visually and/or audibly output the therapy content from the patient device.

20. The system of claim 19, wherein the therapy content comprises a learning module that includes one or more therapy lessons the patient has to complete during a duration of the digital therapeutic, the one or more therapy lessons corresponding to a cognitive behavioral therapy learning portion of the digital therapeutic for treating the underlying disease or disorder.

* * * * *